(12) United States Patent
Bendre et al.

(10) Patent No.: US 8,480,684 B2
(45) Date of Patent: Jul. 9, 2013

(54) RADIATION THERAPY TATTOOING SYSTEM FOR PATIENT POSITIONING

(76) Inventors: Dhananjay Deodatta Bendre, Naperville, IL (US); Andrae L. Parks, Saint Charles, IL (US)

( * ) Notice: Subject to any disclaimer, the term of this patent is extended or adjusted under 35 U.S.C. 154(b) by 410 days.

(21) Appl. No.: 12/400,771

(22) Filed: Mar. 9, 2009

(65) Prior Publication Data

US 2010/0004532 A1    Jan. 7, 2010

Related U.S. Application Data

(60) Provisional application No. 61/068,618, filed on Mar. 7, 2008.

(51) Int. Cl.
*A61B 6/04* (2006.01)
(52) U.S. Cl.
USPC ............................................... 606/116
(58) Field of Classification Search
USPC ............... 606/116, 1, 126, 186; 33/511–513, 33/562–563, 732, 751; 132/319, 320; 602/47, 602/42, 48; 600/414, 420, 431; 401/196; 604/304–308; 424/443, 449
See application file for complete search history.

(56) References Cited

U.S. PATENT DOCUMENTS

| | | | | |
|---|---|---|---|---|
| 3,526,566 | A | * | 9/1970 | McIlvain, Jr. et al. ......... 428/121 |
| 4,876,136 | A | * | 10/1989 | Chang et al. .................. 428/130 |
| 5,163,581 | A | * | 11/1992 | Lombardi, Jr. ................ 221/256 |
| 5,918,608 | A | * | 7/1999 | Renna ........................... 132/320 |
| 5,928,797 | A | * | 7/1999 | Vineberg ....................... 401/132 |
| 2007/0203504 | A1 | * | 8/2007 | Denny et al. .................. 606/116 |

* cited by examiner

*Primary Examiner* — Elizabeth Houston
*Assistant Examiner* — Anh Dang
(74) *Attorney, Agent, or Firm* — Brian A. Gomez; Gomez Int'l Patent Office, LLC

(57) ABSTRACT

The present invention provides a three section skin marking system combining target placement, lancing, marking, cleanup and protective bandaging comprising a positioning target, an ink application pad and a bandage pad, wherein the ink application pad is attached to the positioning target and the bandage pad is attached to the positioning target, wherein the positioning target is an appliqué with a top side and a bottom side and a peripheral border of material with a center portion of the appliqué removed and free of material, wherein the bottom side has an adhesive for adhering to skin of a patient; wherein the application pad comprises an absorbent pad surrounding micro-encapsulated or macro-encapsulated ink for marking the patient's skin; and wherein the bandage pad comprises an absorbent pad and an adhesive strip.

5 Claims, 1 Drawing Sheet

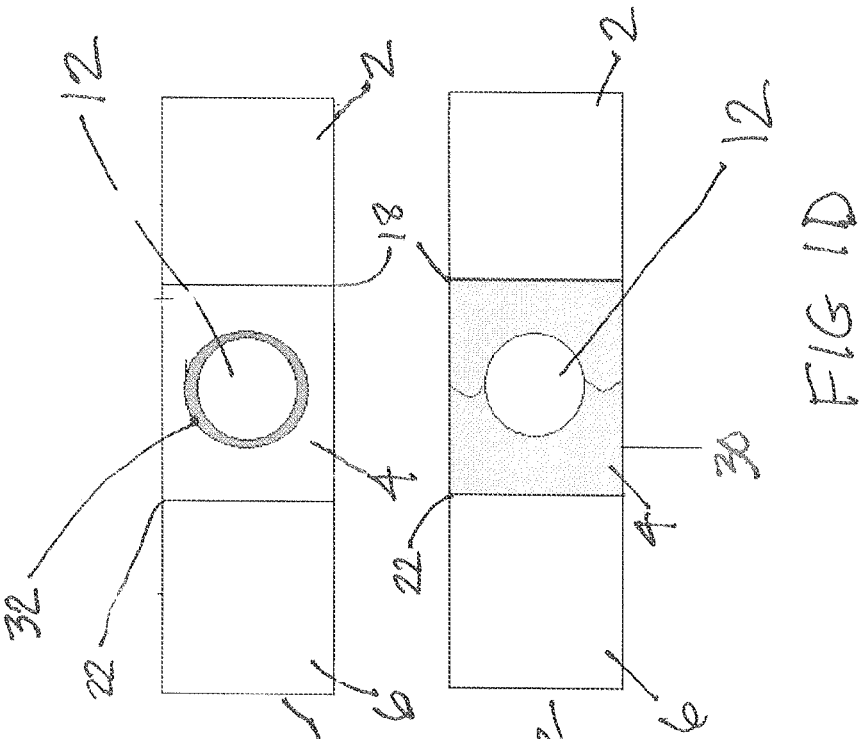
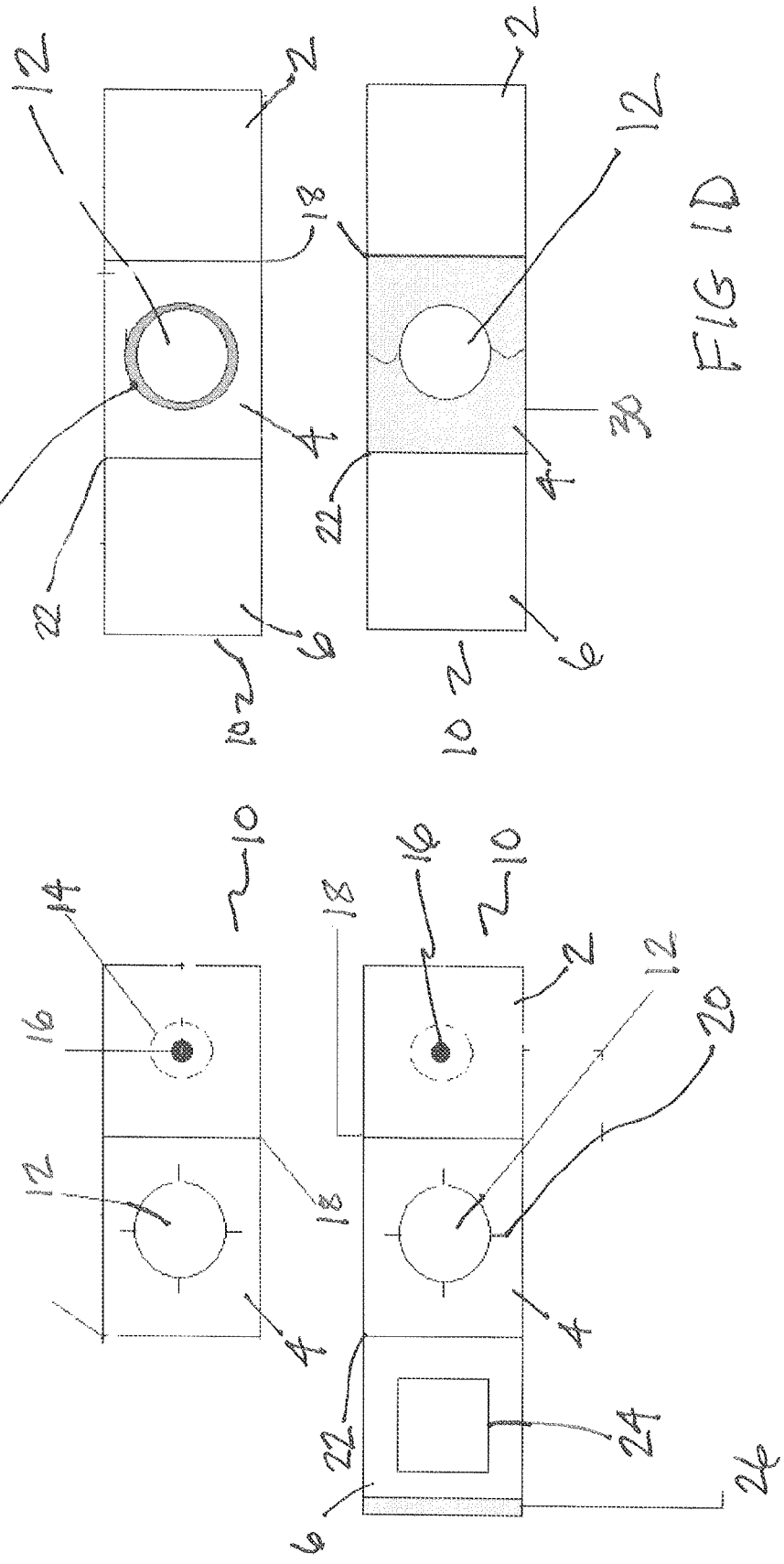

RADIATION THERAPY TATTOOING SYSTEM FOR PATIENT POSITIONING

CROSS-REFERENCE TO RELATED APPLICATION

This application claims the benefit of pending U.S. Provisional Application No. 61/068,618, filed 7 Mar. 2008.

BACKGROUND OF THE INVENTION

In the past, radiation technology therapists (RTT) used permanent pen skin markings to assist them in positioning patients. These surface markings were useful because they helped the therapists on a daily basis to reposition the patient prior to the radiation treatments. However, the permanent pen skin markings were necessarily large and conspicuous because even large permanent pen markings would easily fade. Often, the patient would remove the marks because they were cosmetically displeasing.

Patient setup inconsistencies inherent in the surface pen marking practice led to the adoption of a "truly" permanent tattooing practice. Three pin-head sized positioning tattoos assisted the RTT in putting the patient in the correct position prior to treatment. The tattoo marks were permanent, less conspicuous and cosmetically more appealing than permanent pen marks.

The permanent positioning tattoos are created by placing a drop of dark blue or black India ink on the skin and then using a sterilize needle to implant a small amount of the ink within the skin layer. During the tattooing process the patient may experience a pinprick sensation. This is usually less painful than an experience of a blood draw. Each tattoo is often smaller than a freckle, which, in most cases, would not be seen by anyone other then the patient and RTT.

Presently, most cancer centers use tattoos because tattoos are the best way to position patients for consistent radiation treatment and tattoos are a permanent physical documentation that a patient has had radiation therapy. Furthermore, positioning tattoos assist in consistently positioning the patient so that there is no rotation or translation during the patient set up. In light of today's On board Imaging ("x-ray") and Portal Imaging ("Mega Voltage") technology, tattoos not only help to define the proper alignment for treatment but also assist in keeping imaging (and consequently radiation exposure) to a minimum.

However, present tattooing systems and method suffer from various drawbacks. Thus, there is a need for a simple, clean, sterile and efficient system and method for applying tattoos to patients. The present invention addresses the above drawbacks and provides an elegant solution to patient marking.

SUMMARY OF THE INVENTION

The Isocenter Targeting System (ITS) was developed to provide an effective, time efficient, reproducible and sterile process for placing permanent positioning tattoos on patients without the associated mess and time requirements of the present tattooing practice in radiation therapy. The ITS system is similar to a band aid and is capable of placing a permanent positioning tattoo on the skin. ITS is comprised of two or three parts that are placed in a two-fold or three-fold adhesive strip that are delineated by a perforated border to enable easy separation. Each component plays an important role in the tattooing process.

Specifically, the present invention provides a skin marking system combining target placement and marking comprising a positioning target and an ink application pad wherein the positioning target is an appliqué with a top side and a bottom side, wherein the appliqué has a peripheral border of material and a center portion of the appliqué removed and free of material, and wherein the bottom side has an adhesive for adhering to skin of a patient; and wherein the ink application pad comprises an absorbent pad and ink for marking the patient's skin.

In another embodiment, the present invention provides a three section skin marking system combining target placement, lancing, marking, cleanup and protective bandaging comprising a positioning target, an ink application pad and a bandage pad, wherein the ink application pad is attached to the positioning target and the bandage pad is attached to the positioning target, wherein the positioning target is an appliqué with a top side and a bottom side and a peripheral border of material with a center portion of the appliqué removed and free of material, wherein the bottom side has an adhesive for adhering to skin of a patient; wherein the application pad comprises an absorbent pad surrounding microencapsulated ink for marking the patient's skin; and wherein the bandage pad comprises an absorbent pad and an adhesive strip.

The present invention also provides a method of marking a patient with a tattoo comprising a method of marking a patient comprising the steps of: determining a desired location for marking on a patient's skin; preparing the skin surface for marking; removing the adhesive strip and placing a positioning target of the three section skin marking system of claim 16 around the desired location; folding the ink application pad over the positioning target; lancing the desired location of the patient's skin through the ink application pad; applying pressure to the application pad thereby releasing the ink; unfolding and removing the ink application pad; and folding the bandage pad over the positioning target and adhering the bandage pad to the patient thereby covering and protecting the marked area.

BRIEF DESCRIPTION OF THE DRAWINGS

FIG. 1A illustrates a front view of the two part of the tattoo system of the present invention.

FIG. 1B illustrates a front view of the three part tattoo system of the present invention.

FIG. 1C illustrates a rear view of the three part tattoo system of the present invention.

FIG. 1D illustrates a rear view of the three part tattoo system of the present invention.

DETAILED DESCRIPTION OF THE INVENTION

In marking a patient with a tattoo of the present invention, the patient's skin is prepared in any well know sterilization method. One simple and effective method is the use of a sterile alcohol wipe. Once the general area is sterilized, a precise location is then defined by any well known method. One such method is utilizing room lasers for accurate target location.

After the precise location on the patient has been established, a radiation technology therapist applies the targeting system (ITS) 10 of the present invention. The ITS 10 is either a two-part or three-part system. The system resembles a band aid and can be constructed of any suitable material. A two part system is shown in FIG. 1A and comprises a T-Derm section 4 and a T-Mark section 2. The T-Derm 4 further comprises a target area 12 which is an open area in the center of the T-Derm section 4. For accurate positioning, one can include one or more directional lines or cross-hairs 20 on the periphery of the opening and surrounding the target area 12. While the present figures illustrate the target as a circle, any suitable size or shape is acceptable provided it provides direct access to the patients' skin. A preferred target area 12 can be an opening approximately 2 cm in diameter located in the center of middle of the T-Derm.

As shown in FIGS. 1C and 1D, the rear of the ITS 10 comprises an adhesive liner 30 that covers the T-Derm section 4 and surrounds the target area 12. Surrounding the target area 12 is any suitable robust adhesive for attaching the ITS 10 to the patient.

The RTT removes the adhesive liner 30 from the T-Derm exposing the adhesive surround the target 12 and places the T-Derm 4 on the skin over the area to be tattooed. The directional lines 20 that define the target help the RTT locate the exact spot to be tattooed. Once the T-derm 4 has been placed in position, in one embodiment of the present invention, the RTT lances the skin with a sterile needle device.

The T-Mark 2 is a sterile ink pad assembly with an absorbent pad 14 with India ink 16. In a preferred embodiment, the ink has been micro-encapsulated or macro-encapsulated 16. Once the patient's skin has been lanced, then the sterile T-Mark 2 is folded over the T-Derm 2, thereby covering the target and the lanced area. Once the T-Mark 2 is in contact with the patient's prepared skin, the RTT applies a pressure to release the ink 16 from the pad 14. This process is the key to producing a tattoo on the patient's skin. Once the ink is released it will fill the void in the skin that was produced by the needle device. The micro-encapsulated or micro-encapsulated ink 16 is released and transferred easily to the patient's lanced surface which leads to an uptake that will produce a permanent positioning tattoo.

Once the skin has been marked, the T-Mark 2 can be removed. In the two-part system embodiment, the T-Mark 2 and the T-Derm 4 are separated by a perforated border 18 in the ITS 10. The T-Mark 2 is easily separated from the T-Derm 4 and can be discarded. The T-Derm 4 can be removed at this stage or left on the skin. Whether the T-Derm 4 is removed or remains, the RTT can apply a bandage to protect the lanced area.

The ITS works in a similar fashion in the three-part embodiment. As shown in FIGS. 1B-1D, the third portion of the ITS is the T-Pad 6 which comprises an absorbent pad 24 and an adhesive strip 26. The T-Pad 6 functions as a cleanup pad and protective bandage. In the last and final step using the ITS includes folding the T-Pad 6 over the T-Derm 4. This step is the cleanup phase of the system. The RTT checks that a positioning tattoo has been produced in the prior two steps by unfolding the T-Mark 2. Once the positioning tattoo has been verified by the RTT, the T-Mark 2 can be separated along the perforated border 18 and discarded. The RTT then folds the T-Pad 6 along the perforated border 22 and covers the target opening 12 with the T-Pad 6. The absorbent pad 24 of the T-Pad 6 absorbs any blood or residual ink and acts as a protective bandage over the lanced skin. The edge of the T-Pad includes an adhesive strip 26 for securing to the T-Derm 4 or the patient's skin. In one preferred embodiment, one can use an antibiotic coated T-pad.

Several ink delivery means are contemplated by the present invention. For example, the thimble variation has a reservoir of liquid ink that is placed next to the skin directly on top of the intended needle puncture site. Once the reservoir is in the correct position, the RTT lances the skin through this reservoir where upon the needle carries a small amount of ink depositing it under the skin and producing a permanent positioning tattoo.

The Pellet Variation consists of a pellet of dry ink on the tip of the lancing needle. The lancing procedure performed by the RTT leaves behind the pellet of ink in the lanced skin thus producing a permanent positioning tattoo.

The Drop Variation consists of a drop of ink on the tip of the lancing needle. The lancing procedure performed by the RTT leaves behind the drop of ink in the lanced skin thus producing a permanent positioning tattoo.

The Powder Ink Variation has a disc of dried ink that is placed next to the skin directly on top of the needle puncture site. The lancing procedure performed by the RTT is necessarily more invasive as it has to be deep enough to draw blood. The disc of dried ink dissolves into the blood and comes into contact with the lanced skin and thus produces a permanent positioning tattoo.

The Wet Blister Variation has a reservoir of liquid ink in a small fragile blister that is placed next to the skin directly on top of the needle puncture site. Once the blister is in the correct position, the RTT places some pressure on it which leads to the ink being release. The ink comes into contact with the lanced skin and thus produces a permanent positioning tattoo. One alternative embodiment with the wet blister variation is more robust and designed to be punctured with a lance. The Dry Blister Variation has a reservoir of liquid in a small fragile blister that is directly next to a disc of dry ink. The blister-disc unit is placed next to the skin directly on top of the needle puncture site. Once the blister is in the correct position, the RTT places some pressure on it which leads to the liquid being released and reconstituting the ink. The reconstituted ink comes into contact with the lanced skin and thus produces a permanent positioning tattoo.

The Wet Ink Pad Variation has an pad of wet ink that is placed next to the skin directly on top of the needle puncture site. Once the wet pad comes into contact with the lanced skin it produces a permanent positioning tattoo.

All of the variations can be further modified by using ink that is not visible under normal circumstances. This ink is only visible under special lighting conditions, such as ultra violet, that the RTT uses. A special lighting device is part of this variation. This ink is important for patients who need tattoos on the face, patients who don't want visible tattoos or those patients who have darker skin where normal ink is difficult to see.

The I.T.S. system allows the RTT to place tattoos on the patient's skin without the mess and time requirements associated with the existing tattooing practice. It is a two or three fold system that uses a central open area 12 for target placement, ink transfer pad T-Mark 2 and the T-Pad 6 for clean up and protecting the tattoo area. The integrated three fold system provides the RTT and patient with an effective, time efficient, reproducible and sterile process for the placement of permanent positioning tattoos.

The invention is further defined by the following claims.

We claim:

1. A three section skin marking system combining target placement, lancing, marking, cleanup and protective bandaging comprising a positioning target, an ink application pad and a bandage pad, wherein the ink application pad is attached to the positioning target and the bandage pad is attached to the positioning target, wherein
the positioning target is an appliqué with a top side and a bottom side and a peripheral border of material with a center portion of the appliqué removed and free of material, wherein the bottom side has an adhesive for adhering to skin of a patient;

wherein the application pad comprises an absorbent pad surrounding micro-encapsulated or macro-encapsulated ink for marking the patient's skin; and wherein the bandage pad comprises an absorbent pad and an adhesive strip.

2. The three section skin marking system of claim 1 wherein the ink application pad and the bandage pad are attached with perforations and are detachable.

3. The three section skin marking system of claim 1 wherein each of the three sections is sterilized.

4. The three section skin marking system of claim 1 wherein the bandage pad is an antibiotic coated pad.

5. The three section skin marking system of claim 1 wherein the ink application pad includes ink in the form of at least one selected from the group consisting of thimble, pellet, drop, powder ink, wet blister, dry blister, wet ink pad and invisible ink.

* * * * *